US009700490B2

(12) United States Patent
Walker, Sr. et al.

(10) Patent No.: US 9,700,490 B2
(45) Date of Patent: Jul. 11, 2017

(54) COUGH CONTAINMENT APPARATUS

(71) Applicants: Alan Dewayne Walker, Sr., San Jose, CA (US); Patrice Cassell Walker, San Jose, CA (US)

(72) Inventors: Alan Dewayne Walker, Sr., San Jose, CA (US); Patrice Cassell Walker, San Jose, CA (US)

( * ) Notice: Subject to any disclaimer, the term of this patent is extended or adjusted under 35 U.S.C. 154(b) by 297 days.

(21) Appl. No.: 14/545,123

(22) Filed: Mar. 30, 2015

(65) Prior Publication Data

US 2016/0287483 A1 Oct. 6, 2016

(51) Int. Cl.

| | |
|---|---|
| ***A61B 19/00*** | (2006.01) |
| ***A61J 19/00*** | (2006.01) |
| ***A41B 15/00*** | (2006.01) |
| ***A41D 20/00*** | (2006.01) |

(52) U.S. Cl.

CPC ............... *A61J 19/00* (2013.01); *A41B 15/00* (2013.01); *A41D 20/00* (2013.01); *A41B 2300/326* (2013.01); *A41B 2300/33* (2013.01); *A41B 2400/34* (2013.01); *A41B 2500/40* (2013.01)

(58) Field of Classification Search

CPC ....... A61J 19/00; A41D 20/00; A41B 2400/34
See application file for complete search history.

(56) References Cited

U.S. PATENT DOCUMENTS

| | | | | |
|---|---|---|---|---|
| 3,719,188 | A | 3/1973 | Fisher | |
| 7,766,014 | B2 | 8/2010 | Piret | |
| 2009/0270831 | A1 | 10/2009 | Mazzone | |
| 2010/0252055 | A1* | 10/2010 | Walker, Sr. | A61J 19/00 128/863 |
| 2011/0083259 | A1* | 4/2011 | Wright | A61J 19/00 4/261 |
| 2014/0182592 | A1* | 7/2014 | Aharoni | A61M 16/0045 128/205.25 |
| 2014/0251348 | A1* | 9/2014 | Lemchen | A61C 7/125 128/861 |
| 2015/0013681 | A1* | 1/2015 | Stockhamer | A41B 15/00 128/206.14 |
| 2015/0327603 | A1* | 11/2015 | Roberson | A41B 15/00 128/863 |

* cited by examiner

*Primary Examiner* — Kristen Matter
(74) *Attorney, Agent, or Firm* — Chen-Chi Lin

(57) ABSTRACT

A laminated, antiviral and silver impregnated, 100% activated woven carbon cloth is fashioned into a biodegradable disposable device. The device has the ability to capture and kill viruses, germs and bacteria that emanate from the cough as one suffers the effects of respiratory infections. The device attaches to the wrist and is to be used at first signs of respiratory infection, such as the cold or flu. When one begins to cough, the idea is to press your mouth against the device and deliver the cough instead of coughing into ones hands, sleeve or open air. The carbon base device is antiviral, anti-germ and antibacterial inside and out and will remain effective throughout the entire bout of the cold or flu and is then disposed of. The cough containment apparatus provides security to its users and others, in knowing that the virus is being contained.

9 Claims, 3 Drawing Sheets

COUGH CONTAINMENT APPARATUS

CROSS-REFERENCE TO RELATED APPLICATION

This application incorporates by reference the entire contents of U.S. Ser. No. 12/798,471 filed Apr. 3, 2010.

Not Applicable

BACKGROUND OF THE INVENTION

This application relates to cough containment; specifically pertaining to cough due to the common cold, influenzas (flu), and any contagious respiratory viruses, germs or bacteria.

DISCUSSION OF RELATED ART

There are a number of cough containment devices known in the art. For example: (U.S. Pat. No. 3,719,188) to Fisher, (U.S. Pat. No. 2009/0270831) to Mazzone and (U.S. Pat. No. 7,766,014) to Piret. The development of these few approaches to reduce the spread viruses, germs and bacteria from coughing, have significant shortcomings. These short coming are:

Fisher's cough device claims the prevention of airborne transmission due to the cold or flu, I feel this claim is vague and broad. This device is also cumbersome and the design is complicated. It is impractical to keep the device in one's pocket (assuming one has a pocket) sealed with a top. When suffering the effects of the cold or flu, one cannot control the frequency of the cough, therefore, this forces the user to keep the device in hand.

Fisher teaches a cough device that is specifically designed to contain airborne transmission of the cold or flu. However, Fisher does not teach the killing of viruses, germs and bacteria. Thus, a cough containment apparatus is needed that is more convenient, practical, and efficient in delivering the cough; an apparatus that is made of laminated, antiviral and silver impregnated, 100% activated woven carbon cloth that kills viruses, germs and bacteria.

Mazzone's cough germ containment device (U.S.2009/0270831), overcame many of the shortcomings of Fisher's device through the teaching of a gas permeable antibacterial material for his containment liner. He also teaches the use of biodegradable material to construct his device. He then added a lanyard so that the device may be hung around one's neck for quick access.

Although Mazzone's device is much more effective and efficient than Fisher's Invention, there is yet much room for improvements. Thus, a cough containment apparatus is needed that offers a better delivery system and is more effective in killing viruses. Attaching the apparatus to the wrist gives the wearer a more natural reaction to the cough, since one usually raises one's hand or arm to cover the mouth.

Mazzone's device requires one to grab the apparatus that dangles from the neck and lift it to the mouth. This device may also flop around uncontrollably while the user goes about their daily activities and may become an eyesore or even a choking hazard if one falls asleep while wearing it. Thus, a cough containment apparatus is needed that is more discreet, less visible, and away from the neck and face.

Another shortcoming of Mazzone's invention is that the wearer must wrap his or her mouth around the device, possibly contaminating its rim. If the cough is hurried and misplaced, the outside of the device where there is no antibacterial material, may become contaminated. Wearing the device around the neck puts the virus in close proximity to the face where recontamination is possible.

Despite the broad claims of Mazzone's patent, such as, "gas-permeable antibacterial and biodegradable materials," he does not teach the use of laminated, anti-viral and silver impregnated, 100% activated woven carbon cloth.

Thus, a cough containment apparatus is needed that is made from laminated, antiviral and silver impregnated, 100% activated woven carbon cloth inside and out. Said carbon cloth greatly reduces the possibility of contaminating the outside of the apparatus.

This also holds true when compared to Piret's patent (U.S. Pat. No. 7,766,014) which is a method for absorbing bodily substances discharged from the mouth and nose. Piret's invention is geared more toward fluid containment rather than killing viruses. The sleeve may be adequate for containing fluids discharged from one's mouth and nose while coughing, but falls short in its ability to contain and kill viruses. Piret's sleeve covers a good portion of the arm leaving much more unprotected material vulnerable to contamination by viruses.

Although the sleeve may absorb and contain fluids from the cough, it may absorb viruses into the unprotected area of the sleeve as well. There is also the likelihood of odors forming after prolonged use of the sleeve.

The use of lavender or eucalyptus scents to cover odors, as Piret teaches, will not be enough to mask the odors if the sleeve is used for long periods of time. Many users may be allergic to such scents, however, if the sleeve is washed as Piret teaches, the oil scents or antibacterial substances will be lost in the wash.

Thus, a cough containment apparatus is needed that is covered in an odorless laminated, antiviral and silver impregnated, 100% activated woven carbon cloth. Said carbon cloth kills viruses, germs and bacteria that causes odors and can retain its carbon base and antiviral properties when washed with a special soap.

Another shortcoming of Piret's invention teaches that in order to keep the sleeve from becoming saturated with moisture, viruses, germs and bacteria and spreading to one's arm, "the sleeve may be manufactured from a layered material." In order to accomplish this no leak seal, the liner would have to be made of a non-breathable material such as plastic. Piret compared her invention to that of a layered material found in sanitary napkins and disposable diapers, both of which contain a thin layer of plastic to contain moisture.

However, it's likely that the plastic liner may not allow the skin underneath the sleeve to breathe as well as it should causing the arm to sweat and possibly making the sleeve uncomfortable to wear for long periods of time. Without the liner, the unprotected portion of the sleeve would be the same as coughing onto an unprotected sleeve.

Thus, a cough containment apparatus is needed that is more practical, compact and does not cover large portions of the arm and has laminated, anti-viral and silver impregnated, 100% activated woven carbon cloth wristbands capable of absorbing and deodorizing sweat and saliva particles.

All of the above related art cough containment devices either teach fluid containment, killing bacteria and germs, muffling the cough or containing airborne transmissions, none of which claim to capture and kill viruses.

The present cough containment apparatus is superior to the above related cough containment devices, thus, offering the user efficiency in delivering the cough into the apparatus that kills viruses, germs, bacteria and eliminates odors.

The present cough containment apparatus accomplishes these superior results due to its advanced laminated, antiviral and silver impregnated, 100% activated woven carbon cloth components. Such cloth is manufactured by Chemviron Carbon's Cloth Division based near Durham, UK, under the brand name Zorflex.

The present cough containment apparatus is a simple invention, inexpensive to manufacture and is much more efficient and effective than the above stated related art devices.

Advantages a) Keeps viruses away from the face and hands avoiding contamination.
b) Can be worn almost anywhere without drawing unwanted attention.
c) Is a discrete, hygienic and comfortable way to contain the cough.
d) Kills influenza A and B, H1N1 and many other respiratory viruses.
e) Greatly reduces viruses, germs and bacteria's ability to multiply and spread.
f) May reduce the number of people that get sick each year.
g) Provides containment for respiratory viruses.
h) May help control flu pandemic outbreaks.
i) Reduces the transfer of viruses, germs and bacteria's through touch.
j) Reduce the ability of the virus to multiply after the apparatus is discarded.
k) Can be used by persons of almost any age.
l) Offers multiple levels of protection.
m) Is non-invasive.

These and other advantages will become apparent in the ensuing specifications.

BRIEF SUMMARY OF THE INVENTION

The present device is a disposable cough containment apparatus that attaches to the wrist, with means of killing viruses, germs and bacteria's which emanate from a cough brought on by respiratory infections. Said cough containment apparatus is to be used at the first signs of a respiratory infection, such as a cold or flu. When one begins to cough, the idea is to press your mouth against the cough containment apparatus and deliver the cough instead of coughing into one's hands, sleeve or into the open air.

Figure 1:
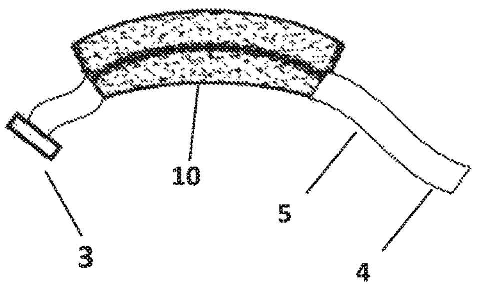
FIG. 1, FIG. 1A, FIG. 1B and FIG. 1C show illustrations of the operation of cough containment apparatus 10 and two side views of the interaction of the wristband strap assembly 3, 4 and 5.

a) A perspective view of top carbon cloth 1 in accordance with one embodiment.
b) A perspective view of bottom carbon cloth 1A in accordance with one embodiment.
c) A perspective view of strap ring 3 in accordance with one embodiment.
d) A perspective view of hook fastener 4 in accordance with one embodiment.
e) A perspective view of loop fastener 5 in accordance with one embodiment.
f) A perspective view of rectangle box frame 2 in accordance with one embodiment.
g) A perspective view of carbon cloth inserts 6 A-E in accordance with one Embodiment.

REFERENCE NUMERALS

In the drawings, some closely related numbers may have the same number but different alphabetic suffixes.

1. Top Carbon Cloth
1A. Bottom Carbon Cloth
2. Rectangle Box Frame
3. Strap Ring
4. Hook Fastener
5. Loop Fastener
6. A-E Carbon Cloth Inserts
10. Cough Containment Apparatus Assembly.

DETAILED DESCRIPTION OF THE INVENTION

One Embodiment

Figure 2:
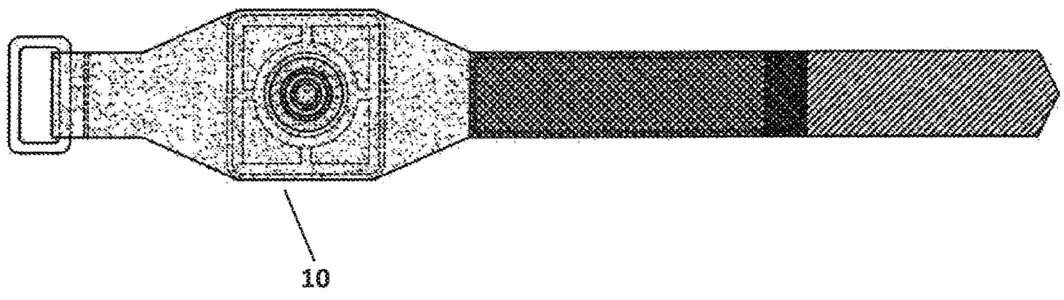
FIG. 2 shows a top view and FIG. 2A shows a side view of the completed cough containment apparatus 10 showing external components and hidden internal components in accordance with one embodiment.
Figure 2A:

FIG. 2 and FIG. 2A show a top and side view of one version of cough containment apparatus 10. Said cough containment apparatus 10 and its components interact as follows: A laminated, anti-viral and silver impregnated, 100% activated woven carbon cloth is cut into three distinct patterns. One top carbon cloth 1, one bottom carbon cloth 1A and five carbon cloth inserts 6A-E. Said top carbon cloth 1 FIG. 3 has a rectangular body with tapered sides and an ample hole in the center.

Said top carbon cloth 1 is fashioned with two wristband straps protruding from opposite sides of the long sides of its rectangular body. One short wristband strap and one long wristband strap.

Figure 1A:
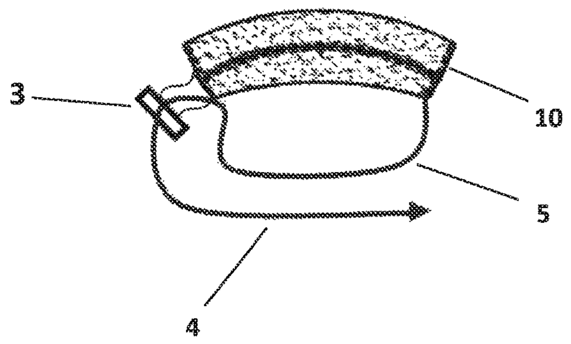
Figure 1B:
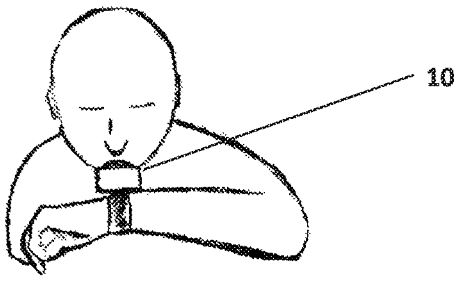
Figure 1C:
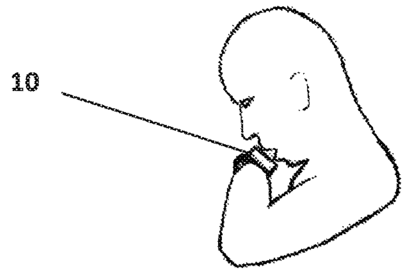
Figure 3:
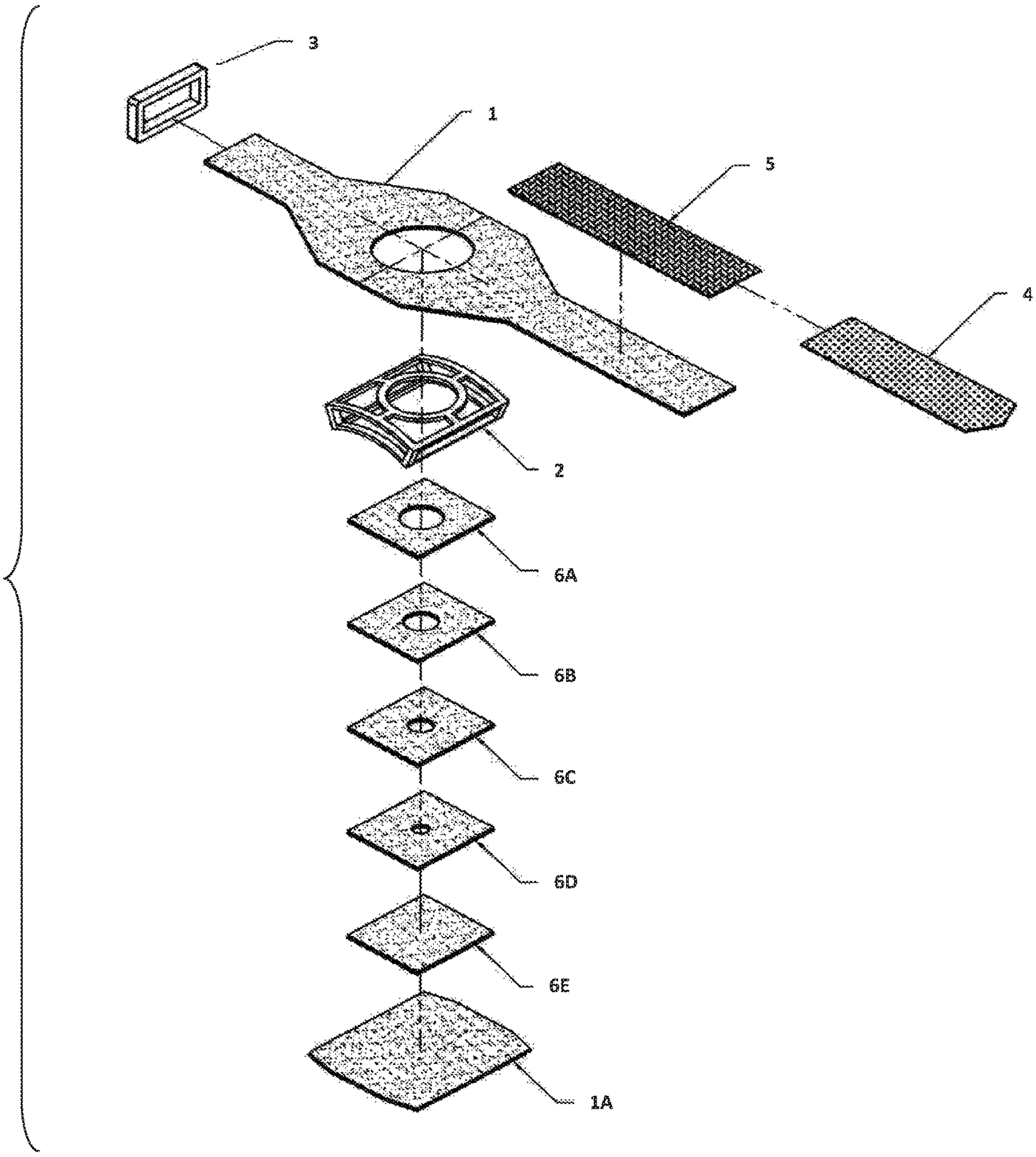
FIG. 3 is an exploded/assembly view of said cough containment apparatus 10 and all of its components as follows.

A hook and loop strap fastener material 4 & 5 of FIG. 3 is sewn to the long wristband strap of said top carbon cloth 1. The short wristband strap of said top carbon cloth 1 is looped; a plastic strap ring 3 of FIG. 3 is placed inside the loop; said loop is closed and sewn together, sealing said plastic strap ring 3 inside. Said hook and loop fastener material 4 & 5 and said strap ring 3 interact with each other; offering means to attach said cough containment apparatus 10 to the wrist (see FIG. 1 and FIG. 1A).

Said bottom carbon cloth 1A has a rectangular body and tapered sides that matches the rectangular body and tapered sides of said top carbon cloth 1, but is fashioned without the ample hole or wristband straps. Said top and bottom carbon cloths are sewn together along three edges creating a pouch or pocket.

A bio-degradable plastic is molded into a ridged stick box frame 2 of FIG. 3. Said frame consists of a rectangular hollow box with an arc shape and toothpick like structure; comprising of, two short sides, two long sides, one top, and an open bottom.

Said short sides of said rectangular box frame 2 is designed with four arcs; two long arcs on top, at opposite sides of the short side of the rectangular box frame and two short arcs on bottom at opposite sides of the short side of the rectangular box frame. Said top and bottom arcs are connected by four short toothpick like sticks. The two different arc lengths causes the two long sides of said rectangular box frame to taper inward creating a slight inward angle. Said bottom arc is designed to match the contour of any size wrist.

The top of rectangle box frame 2 is fashioned with an ample diameter cough ring in the center. Four short toothpick like cross sticks joins said cough ring to said frame and stabilizes the frames entire structure; said frame is designed to fit inside the pouch created by the sewing together of said top and bottom carbon cloth 1 & 1A.

Five carbon cloth inserts 6A-E of FIG. 3 are cut into five equal rectangular shapes, each having different size hole patterns in the center of the cloth. Said carbon cloth inserts 6A-E is stacked one on top of the other, greater hole on top to lesser hole on the bottom. This descending hole pattern creates a funnel effect that allows the cough to penetrate to the lower levels of said carbon cloth inserts. Said five carbon cloth inserts are stacked and inserted inside of said rectangular box frame 2 through its open bottom. Said box frame and said carbon cloth inserts are placed inside the pouch that was created by the sewing together of said top and bottom carbon cloths 1 and 1A.

The ample cough ring of said rectangular box frame 2 is designed to align with the ample hole of said top carbon cloth 1; offering means to deliver the cough into said cough containment apparatus 10. The fourth side of the pouch is sewn together sealing said frame and said carbon cloth inserts inside, completing the cough containment apparatus 10 of FIG. 2 and FIG. 2A.

Operation

One Embodiment

The Cough containment apparatus is the first of its kind to offer a laminated, antiviral and silver impregnated, 100% activated woven carbon cloth.

Cough containment apparatus 10 of FIG. 2 and FIG. 2A is a disposable apparatus which attaches to the wrist like a wristwatch, offers a discreet yet effective means of containing ones cough as shown in the illustration of FIG. 1, FIG. 1A, FIG. 1B and FIG. 1C.

The Object(s) of my invention is to contain airborne pathogens, respiratory secretions, viruses, germs and bacteria which emanate from the cough as one suffers the effects of respiratory infection.

FIG. 3 is an exploded view of cough containment apparatus 10 showing all of its components as follows:

FIG. 3 shows a perspective view of said top carbon cloth 1 and bottom carbon cloth 1A of said cough containment apparatus 10. Said carbon cloth is a laminated, antiviral, and silver impregnated 100% activated woven carbon cloth. The impregnation of silver gives the cloth its antiviral properties. The 100% activated carbon kills germs and bacteria that cause odors. Said carbon cloth is micro porous which absorbs fluids and sweat which may occur from prolonged use of the cough containment apparatus.

FIG. 3 also shows a perspective view of rectangle box frame 2. Said box frame consist of an arc shaped hollow plastic stick support structure. Said rectangle box frames arc shape design match the contour of any size wrist. The hollow box stick frame and carbon cloth offers little resistance to the pressure created by the cough allowing maximum dispersal of the pressure.

FIG. 3 also shows a perspective view of the stacked carbon cloth inserts 6A-E with descending hole patterns. Said carbon cloth inserts are made from laminated, antiviral and silver impregnated, 100% activated woven carbon cloth.

FIG. 3 also shows a perspective view of the strap assembly. Hook fastener 4, loop fastener 5 and strap ring 3 interact as follows: Said cough containment apparatus 10 is placed on the back of the wrist. Hook and loop fasteners 4 & 5 is wrapped around the inside of the wrist and inserted through the opening in strap ring 3 and pulled back in the opposite direction; as seen in the illustration of FIG. 1, FIG. 1A, FIG. 1B and FIG. 1C, enabling said wristband to tightening around the wrist. Once desired tightness is obtained said hook and loop fasteners are pressed together securing said cough containment apparatus to the wrist.

Said cough containment apparatus accomplishes its results due to its advanced laminated, antiviral and silver impregnated, 100% activated woven carbon cloth components. Cough containment apparatus 10 will bring security to users, as well as others, in knowing that the viruses, germs and bacteria are being contained.

Conclusion, Ramifications, and Scope

Accordingly, the reader will see in the ensuing specifications how various embodiments can be used to accomplish the same results.

Alternative embodiments for cough containment apparatus 10 includes but is not limited to:

a) Some embodiments of cough containment apparatus 10 can be designed to be worn on the back of the hand or side of the wrist Alternative embodiments for laminated, anti-viral and silver impregnated, 100% activated woven carbon cloth 1, 1A & 6A E of FIG. 3 includes but is not limited to:

a) The wristbands of top carbon cloth 1 can be made from textiles without the use of carbon or impregnation of silver.
b) Bottom carbon cloth 1A can be made from textiles without the use of carbon or impregnation of silver.
c) Can be non-woven or knitted.
d) Can be made from impregnated carbon paper.
e) Said laminate can come in various colors.
f) Said metal impregnation can be copper or other anti-viral metals.
g) Said impregnation can be any type of antiviral substance or materials.

Alternative embodiments for said rectangle box frame 2 of FIG. 3 includes but is not limited to:

a) Pressed cardboard.
b) Paper mash a.
c) Vinyl.
d) Nylon.
e) Laminated or impregnated fibrous materials.
f) Various plastic zed materials or any material ridged enough to hold said contents in place.

Some embodiments can be constructed using no container frame at all. By inserting said carbon cloth inserts into the sewn pouch of item 1 & 1A without said box frame.

Alternative embodiments for said strap ring 3 includes but not limited to:

a) pressed cardboard.
b) paper mash a.
c) vinyl.
d) nylon.
e) laminated or impregnated fibrous materials.
f) various plastic zed materials, or any material ridged enough to support said hook and loop straps 4 & 5.

All said alternative embodiments can be made from recycled materials. While the above description contains many specificities these should not be construed as limitations on the scope, but rather as an exemplification of several embodiments.

SEQUENCE LISTING OR PROGRAM

Not Applicable

I claim:

1. A disposable cough containment apparatus comprising:

a top cloth, said top cloth comprising:

a rectangular body with tapered sides;

an ample hole in a center of the top cloth; and two wristband straps for securing the disposable cough containment apparatus to a wrist;

a bottom cloth, said bottom cloth secured to the top cloth along edges of the top and bottom cloths to create a pouch;

a plurality of rectangular carbon cloth inserts having a plurality of holes, each cloth insert of the plurality of rectangular carbon cloth inserts having a respective hole of the plurality of holes in a center of said each cloth insert, the respective hole of said each cloth insert being of a different size from any other hole of the plurality of holes in any other carbon cloth insert of the plurality of rectangular carbon cloth inserts, the plurality of rectangular carbon cloth inserts being stacked in a descending order from a cloth insert of the plurality of rectangular carbon cloth inserts with a largest hole of the plurality of holes to a cloth insert of the plurality of rectangular carbon cloth inserts with a smallest hole of the plurality of holes; and a plastic frame for fitting inside the pouch, said plastic frame comprising:

two short sides;

two long sides;

a top with an ample diameter cough ring in a center of the top; and an open bottom;

wherein each short side of said two short sides has a respective long arc on a top of said each short side and a respective short arc on a bottom of said each short side, wherein said long and short arcs cause the two long sides of the plastic frame to taper inward, wherein the short arcs of the two short sides are designed to match a contour of the wrist, and wherein the plurality of rectangular carbon cloth inserts are placed inside the plastic frame through the open bottom;

wherein the ample diameter cough ring of the plastic frame is aligned with the ample hole in the top cloth; and wherein the top cloth, the bottom cloth, and the plurality of rectangular carbon cloth inserts are made from a laminated, antiviral, activated carbon cloth.

2. The disposable cough containment apparatus of claim 1, wherein the top cloth, the bottom cloth, and the plurality of rectangular carbon cloth inserts are made of a woven material.

3. The disposable cough containment apparatus of claim 1, wherein the top cloth, the bottom cloth, and the plurality of rectangular carbon cloth inserts are made of a non-woven material.

4. The disposable cough containment apparatus of claim 1, wherein the top cloth, the bottom cloth, and the plurality of rectangular carbon cloth inserts are made of an impregnated carbon paper material.

5. The disposable cough containment apparatus of claim 1, wherein the top cloth, the bottom cloth, and the plurality of rectangular carbon cloth inserts are of different colors.

6. A disposable cough containment apparatus comprising:

a top cloth, said top cloth comprising:

a rectangular body with tapered sides;

an ample hole in a center of the top cloth; and two wristband straps for securing the disposable cough containment apparatus to a wrist;

a bottom cloth, said bottom cloth secured to the top cloth along edges of the top and bottom cloths to create a pouch; and a plurality of rectangular carbon cloth inserts having a plurality of holes, each cloth insert of the plurality of rectangular carbon cloth inserts having a respective hole of the plurality of holes in a center of said each cloth insert, the respective hole of said each cloth insert being of a different size from any other hole of the plurality of holes in any other carbon cloth insert of the plurality of rectangular carbon cloth inserts, the plurality of rectangular carbon cloth inserts being stacked in a descending order from a cloth insert of the plurality of rectangular carbon cloth inserts with a largest hole of the plurality of holes to a cloth insert of the plurality of rectangular carbon cloth inserts with a smallest hole of the plurality of holes;

wherein the top cloth, the bottom cloth, and the plurality of rectangular carbon cloth inserts are made from a laminated, antiviral, activated carbon cloth.

7. The disposable cough containment apparatus of claim 6, wherein the disposal cough containment apparatus excludes from further comprising a frame.

8. The disposable cough containment apparatus of claim 6, wherein the disposal cough containment apparatus further comprises a frame.

9. The disposable cough containment apparatus of claim 6 further comprising a hook and loop strap fastener material.

* * * * *